US005714123A

United States Patent [19]
Sohrab

[11] Patent Number: 5,714,123
[45] Date of Patent: Feb. 3, 1998

[54] PROTECTIVE SHIELD FOR A BLOOD GLUCOSE STRIP

[75] Inventor: Borzu Sohrab, Los Altos, Calif.

[73] Assignee: Lifescan, Inc., Milpitas, Calif.

[21] Appl. No.: 723,040

[22] Filed: Sep. 30, 1996

[51] Int. Cl.$^6$ ............................................. C12M 1/16
[52] U.S. Cl. ........................... 422/99; 422/55; 422/58; 422/61; 422/104; 422/117; 436/165
[58] Field of Search .......................... 422/55, 58, 61, 422/104, 117, 99; 436/46, 164, 165, 807

[56] References Cited

U.S. PATENT DOCUMENTS

| | | | |
|---|---|---|---|
| 4,827,944 | 5/1989 | Nugent | 128/771 |
| 4,833,088 | 5/1989 | DeSimone et al. | 435/289 |
| 4,952,373 | 8/1990 | Sugarman et al. | 422/99 |
| 5,100,620 | 3/1992 | Brenneman | 422/58 |
| 5,554,531 | 9/1996 | Zweig | 435/286.1 |
| 5,563,042 | 10/1996 | Phillips et al. | 435/14 |
| 5,571,667 | 11/1996 | Chu et al. | 435/5 |
| 5,597,532 | 1/1997 | Connolly | 422/58 |
| 5,622,871 | 4/1997 | May et al. | 436/514 |

*Primary Examiner*—Long V. Le
*Attorney, Agent, or Firm*—James Riesenfeld

[57] ABSTRACT

A modified blood glucose test strip reduces the risk of contamination when it is used with a blood glucose meter. The modified strip has adhered to its top surface a protective shield that is preferably cut from a sheet of transparent plastic. The shield permits access to the sample-receiving surface of the strip, but prevents contamination of the meter by the user, because it covers a part of the meter that adjoins the strip when the strip is installed in the meter. Similarly, the shield protects a user from contacting a potentially contaminated area of the meter. The modified strip finds particular advantage in a hospital or other setting where several persons may use the same meter.

5 Claims, 4 Drawing Sheets

PROTECTIVE SHIELD FOR A BLOOD GLUCOSE STRIP

BACKGROUND OF THE INVENTION

1. Field of the Invention

This invention relates to a modified blood glucose strip; more particularly, to a blood glucose strip with an integral protective shield to reduce the risk of meter contamination.

2. Description of the Related Art

In recent years, the medical diagnostics industry has focused increasing attention on the health risks posed by blood-borne illnesses, such as AIDS and hepatitis. Thus, diagnoses that involve testing blood must minimize the risk of contaminating equipment and personnel with blood from a patient, as well as the risk of contaminating the patient with blood from others.

Among the medical diagnostic devices that are in most widespread use today is the blood glucose monitor. In the U.S. alone, there are an estimated 14 million people with diabetes. In order to avoid serious medical problems, such as vision loss, circulatory problems, kidney failure, etc., many of these people monitor their blood glucose on a regular basis and then take the steps necessary to maintain their glucose concentration in an acceptable range.

Blood contamination is of concern when making a blood glucose measurement. For example, when using the most common types of whole blood glucose meters (photometric), the glucose determination is generally made from a blood sample that is applied to a test strip that is on the meter. To apply the patient's finger-stick blood sample, the patient's finger must be positioned above and near to the test strip in order to inoculate the test strip with the blood sample. There is a risk that the patient's finger may come into contact with a portion of the meter. Although that would not pose a serious health risk when a meter is used by only one person, it may be a problem when the meter is used in a hospital. In that case, there is a potential for cross-contamination. Blood on the meter also poses a potential hazard to healthcare workers.

A number of systems have been disclosed that are aimed at reducing the risk of contamination to a patient and/or to others in connection with diagnostic tests.

U.S. Pat. No. 4,952,373, issued Aug. 28, 1990, to Sugarman et al., discloses a shield that is designed to prevent excess liquid on diagnostic cartridges from being transferred to a monitor with which the cartridge is used. The shield is fabricated from thin plastic or metallic film and is attached to a cartridge that is generally the size of a credit card.

U.S. Pat. No. 5,100,620, issued Mar. 31, 1992, to Brenneman, discloses an inverse funnel shaped body with a central capillary tube to transport a liquid sample from a remote sample-application point to a test surface. The device can be used to transfer blood from a finger stick to a reagent film.

SUMMARY OF THE INVENTION

In accordance with the present invention, a blood glucose monitoring device comprises a) a blood glucose strip of the type that is inserted into a predetermined position in a blood glucose meter and that has a sample-receiving area to which a sample of blood can be applied for a measurement by the meter of a glucose concentration in the sample and b) a protective shield secured to the strip, bounding at least a part of the sample-receiving area, and covering a part of the meter when the strip is in the position.

The device of the present invention permits a person to use a conventional photometric blood glucose meter with on-meter dosing, but with reduced risk that the person will either contaminate the meter or be contaminated by it. The device is disposable, and the terms "device" and "disposable" are used interchangeably throughout this specification and the appended claims.

BRIEF DESCRIPTION OF THE DRAWINGS

FIG. 1 is an exploded perspective view of a device of this invention and a meter that it is used with.

DETAILED DESCRIPTION OF THE INVENTION

Figure 1:
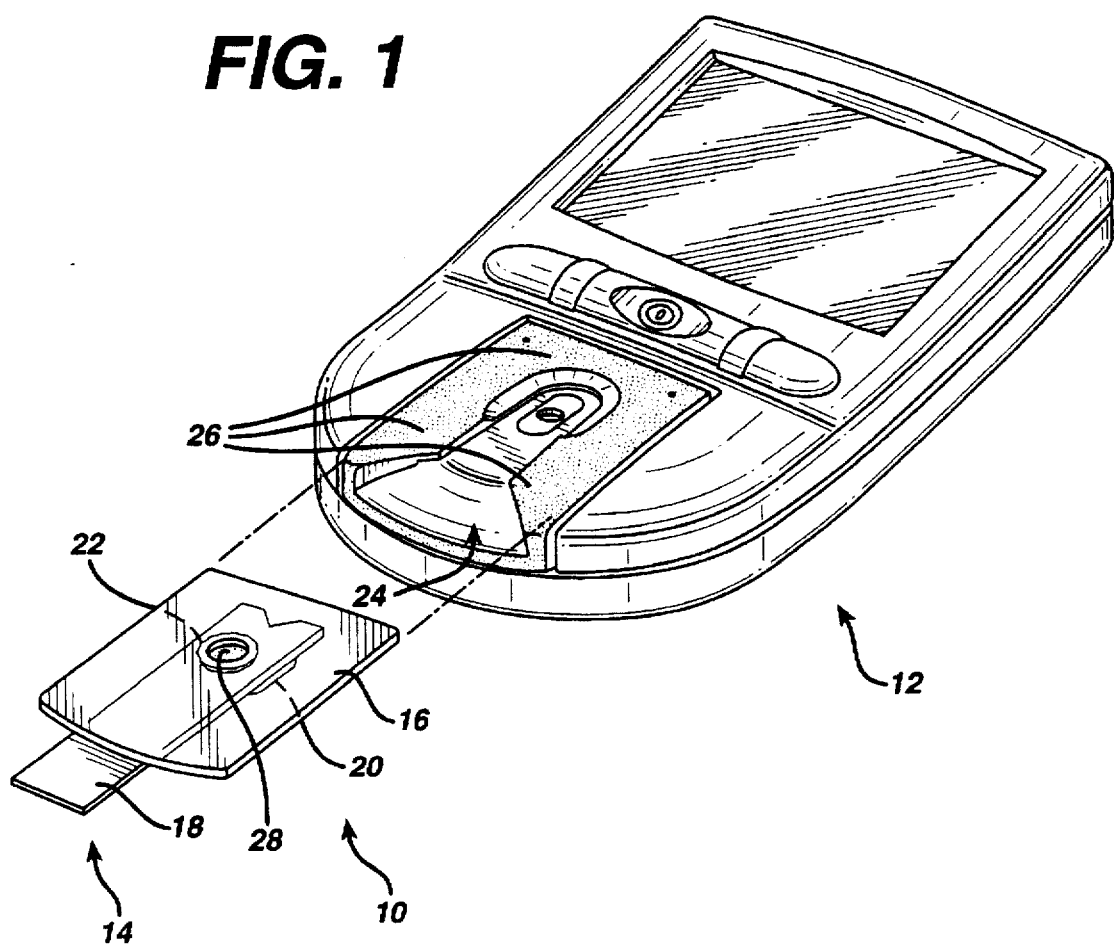

Blood glucose monitors that involve "on-meter dosing" are well known in the art and are typified by the One Touch® group of meters from LifeScan, Inc., Milpitas, Calif. Those meters involve the use of a strip that is impregnated with a reagent that causes a color change that can be related to the glucose concentration in a whole-blood sample applied to the strip. In practice, a user first inserts a blood glucose strip into the meter, and then applies to a designated area on the top ("sample") surface of the strip a sample of his/her blood. As the sample passes through the strip toward the other ("testing") surface, glucose in the sample reacts with the reagent to cause a change in strip reflectance at the testing surface. This change in reflectance can be related to the glucose concentration in the blood sample.

Since persons with diabetes, for whom blood glucose meters are intended, often are visually impaired, they may find it difficult to apply a blood sample from a finger stick onto the designated area on the strip. They may inadvertently touch their blood to a part of the meter, near that designated area on the strip. Thereafter, a later user—who, particularly in a hospital setting, may be a different person—may come into contact with the previous user's blood. The device of the present invention addresses the problems of contamination of blood glucose meters with blood from a user and contamination of a user with (a previous user's) blood from a meter. It does so, by providing a shield, which is secured to the strip, bounds at least a part of the sample-receiving area of the strip, and covers part of the meter when the strip is in position. By stating that the shield "bounds at least a part of the sample-receiving area" we mean that it adjoins part of that area, possibly, but not necessarily, surrounding the area. The primary purpose of the shield is to prevent contamination of the meter with the user's blood, and that purpose does not require the shield to surround the sample-receiving area. If the shield surrounds the area, for example, by incorporating a through hole aligned with the area, it helps the user apply the sample in the proper place. Optionally, the user may be further assisted by a target imprinted on the shield to help locate the area. The target may be a graphic design printed on the shield; for example, a circle or any other kind of assistance pattern applied to the shield. The shield is conveniently secured to the strip by an adhesive that surrounds the through hole. If the shield does not surround the sample-receiving area, then it has a longer edge, along which it is convenient to apply adhesive for bonding to the strip over a larger area. Although any flexible sheet material would be suitable, the shield is preferably cut from a sheet of transparent, flexible plastic. There are a number of well-known thermoplastic materials that are suitable; e.g. polyester, polycarbonate, polystyrene, etc. The thickness is not critical, but is typically in the range from about 0.05 to about 0.2 mm.

FIG. 1 is an exploded perspective view showing a device 10 of the present invention and a meter 12. Device 10 consists of a test strip 14 and shield 16. Test strip 14 includes a holder, or handle, 18 and reagent pad 20. Shield 16 is adhered to holder 18 of test strip 14 with adhesive 22. In use, strip 14 is inserted into slot 24, while shield 16 covers the area 26 that adjoins the slot.

Figure 2:
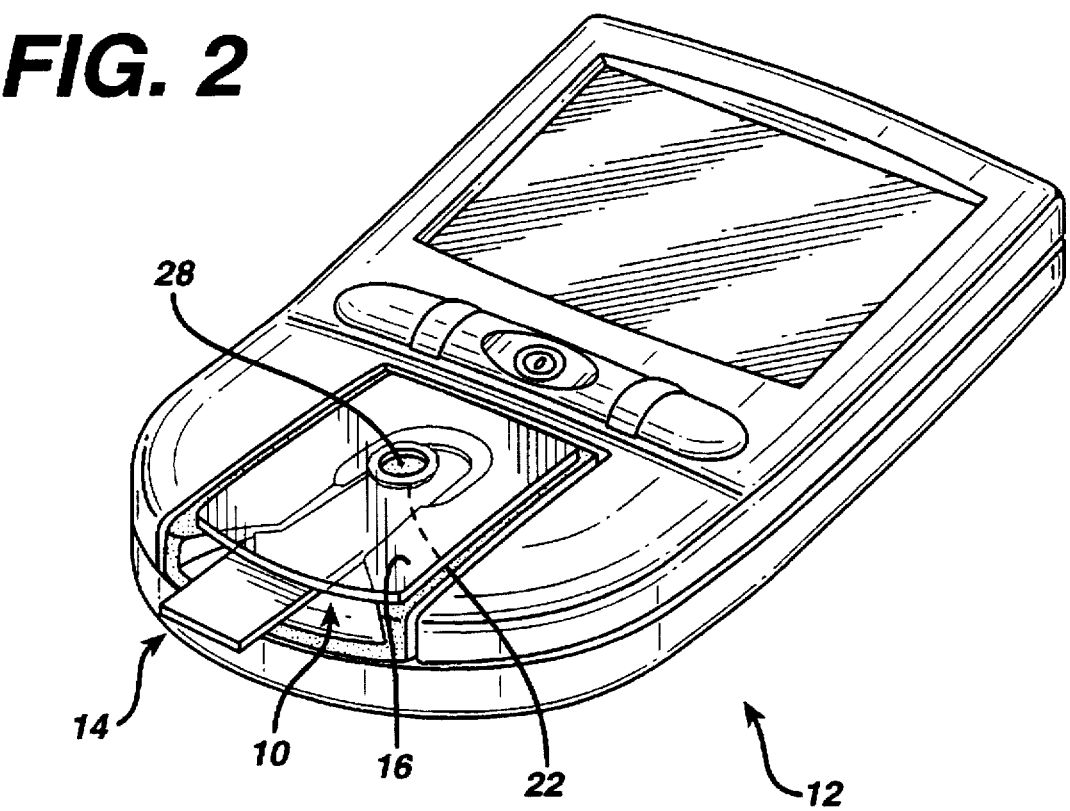
FIG. 2 is a perspective view of the device of FIG. 1 installed in the meter of FIG. 1.

FIG. 2 is a perspective view of the device 10 mounted in meter 12 and ready for a blood sample to be applied to sample-receiving area 28 of strip 14. Area 28 is surrounded by adhesive 22. Shield 16 covers adjoining areas of the meter and presents them from becoming contaminated with blood.

Figure 3:
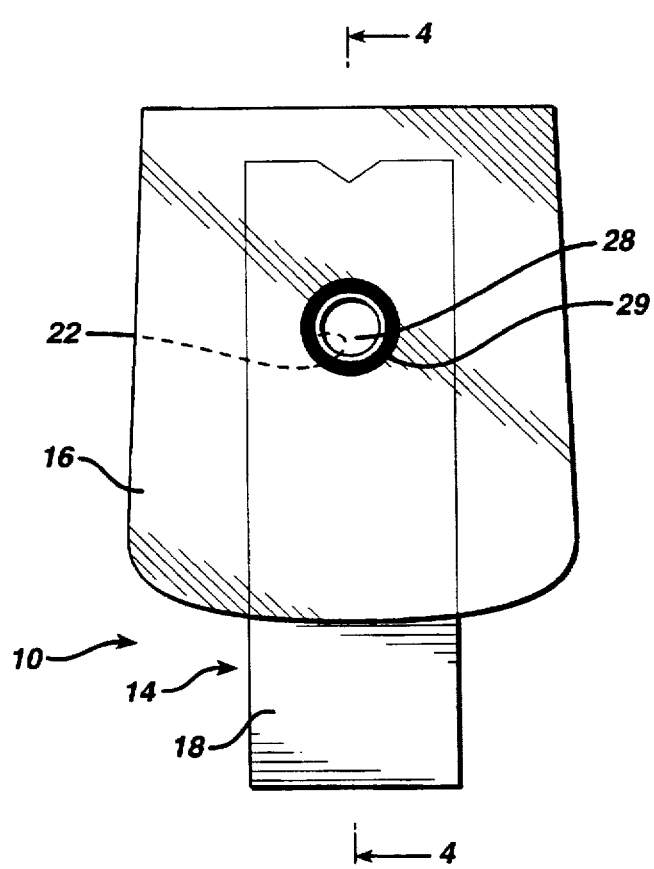
FIG. 3 is a top plan view of a device of this invention.

FIG. 3 is a top plan view of a device 10 of this invention, showing holder 18 of strip 14 adhered with adhesive 22 to shield 16. Optional target 29 surrounds the sample-receiving area 28 of strip 14 to help a user locate that area.

Figure 4:
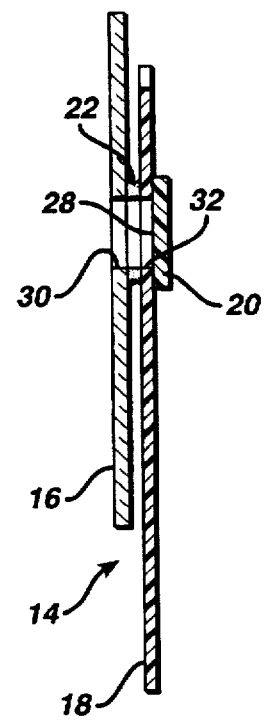
FIG. 4 is a cross-sectional view of the device of FIG. 3.

FIG. 4 is a sectional view of the device of FIG. 3, taken along line 4—4 of FIG. 3. As is dear from FIG. 4, the sample-receiving area 28 of strip 14 is at the top surface of reagent pad 20. Through holes 30 and 32 of shield 16 and holder 18, respectively, are co-aligned over sample-receiving area 28.

Figure 5:
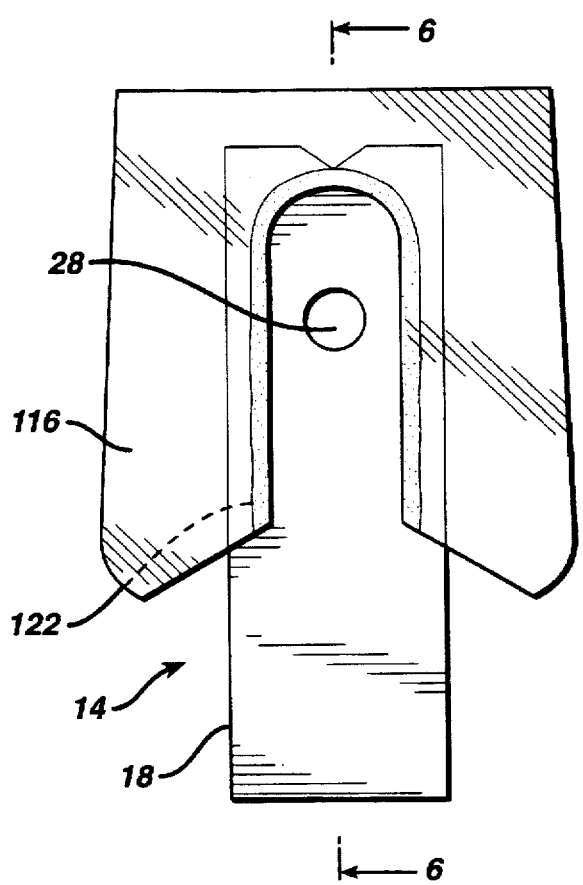
FIG. 5 is a top plan view of an alternative embodiment of a device of this invention.

FIG. 5 is a top plan view of an alternative embodiment of a device of this invention. In the embodiment shown, shield 116 has a U-shaped cutout. Adhesive 122 adheres shield 116 to holder 18 of strip 14 along the perimeter of the cutout.

Figure 6:
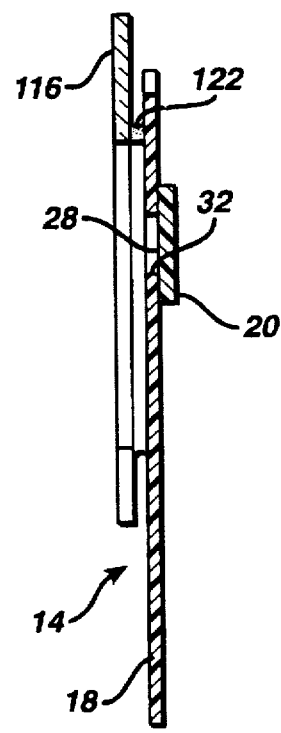
FIG. 6 is a cross-sectional view of the device of FIG. 5.

FIG. 6 depicts a cross section taken along line 6—6 of FIG. 5. Hole 32 of holder 18 overlies sample-receiving area 28 of strip 14, which is at the top surface of reagent pad 20.

It will be understood by those skilled in the art that the foregoing descriptions of embodiments of this invention are illustrative of practicing the invention but are in no way limiting. Variations of the detail presented may be made without departing from the scope and spirit of the present invention.

I claim:

1. A blood glucose monitoring device, comprising
   a. a blood glucose strip for insertion through a slot into a predetermined position in a blood glucose meter and having a sample-receiving area to which a sample of blood can be applied for a measurement by the meter of a glucose concentration in the sample and
   b. a protective shield secured to the strip, bounding at least three sides of the sample-receiving area, and covering a part of the meter that adjoins the slot when the strip is in the position.

2. The monitoring device of claim 1 in which the shield comprises a substantially transparent thermoplastic sheet.

3. The monitoring device of claim 1 in which the shield has a through hole that is substantially aligned with the sample-receiving area.

4. The monitoring device of claim 3 in which the shield is secured to the strip with an adhesive that surrounds the through hole.

5. The monitoring device of claim 3 in which a target imprinted on the shield locates the through hole.

* * * * *